United States Patent [19]

Baines et al.

[11] 4,098,878

[45] Jul. 4, 1978

[54] TOOTHPASTE CONTAINING MILLED ALPHA-ALUMINA TRIHYDRATE

[75] Inventors: Eric Baines, Manchester; Peter Platt, Tottington, Near Bury; Kenneth Tomlinson, Bramhall, all of England

[73] Assignee: Colgate-Palmolive Company, New York, N.Y.

[21] Appl. No.: 625,218

[22] Filed: Oct. 23, 1975

Foreign Application Priority Data

Oct. 29, 1974 [GB] United Kingdom ........ 46827/74

[51] Int. Cl.$^2$ ........................... A61K 7/16; A61K 7/18
[52] U.S. Cl. ........................... 424/52; 51/308; 424/49
[58] Field of Search ..................... 424/49–58; 51/308

[56] References Cited

U.S. PATENT DOCUMENTS

| 1,965,299 | 7/1934 | Patterson | 51/308 |
|---|---|---|---|
| 2,010,910 | 8/1935 | Atkins | 424/49 |
| 2,278,442 | 4/1942 | Heany | 51/308 X |
| 2,417,800 | 3/1947 | Weisser | 51/304 |
| 2,829,035 | 4/1958 | Doughty | 51/304 |
| 3,034,967 | 5/1962 | Apperson et al. | 424/52 |
| 3,060,098 | 10/1962 | Gershon | 424/52 |
| 3,151,027 | 9/1964 | Cooley et al. | 424/52 |
| 3,265,475 | 8/1966 | Schantz | 51/304 |
| 3,325,368 | 6/1967 | Wood | 424/52 |
| 3,662,060 | 5/1972 | Clippendale et al. | 424/57 |
| 3,678,155 | 7/1972 | Clippendale et al. | 424/52 |
| 3,822,345 | 7/1974 | Murray et al. | 424/52 |
| 3,929,987 | 12/1975 | Colodney et al. | 424/52 |
| 3,935,306 | 1/1976 | Roberts et al. | 424/49 |

Primary Examiner—Shep K. Rose
Attorney, Agent, or Firm—Robert L. Stone; Murray M. Grill; Herbert S. Sylvester

[57] ABSTRACT

Dentifrices containing milled alpha-alumina trihydrate which has been surface-treated with a higher fatty acid.

7 Claims, No Drawings

TOOTHPASTE CONTAINING MILLED ALPHA-ALUMINA TRIHYDRATE

One aspect of this invention relates to toothpaste formulations containing sodium fluoride and, as a dental abrasive, milled Bayer process alpha-alumina trihydrate (hereinafter termed "trihydrate"); such milled trihydrate is a well known commercial product. It is found that the trihydrate tends (particularly when it is of a less alkaline type) to react with the sodium fluoride and analysis of the freshly prepared toothpaste gives values of soluble fluoride much lower than when the abrasive is inert. It is also found that the interaction of the trihydrate and the sodium fluoride may be demonstrated by making a slurry of the trihydrate in water (e.g. a slurry containing 20 or 25% of trihydrate), measuring the pH, and then adding an aqueous solution of sodium fluoride, e.g. to provide about two parts by weight of NaF per 100 parts of trihydrate. The pH of such 20% slurry (of the less alkaline type of trihydrate) is generally below 9, such as about 8½; the addition of the NaF results in an immediate rise in pH by well over one pH unit, such as 2 or 3 pH units.

It has been found that pretreating the trihydrate with stearic acid greatly inhibits the reaction of the trihydrate and sodium fluoride. Very little stearic acid is needed. Thus, in one successful embodiment, the proportion of stearic acid was only 1% based on the weight of the trihydrate.

The following Examples illustrate the invention further. In this application all proportions are by weight unless otherwise indicated.

EXAMPLE 1

The milled trihydrate of the less alkaline type in this Example is Alcoa C-333 a product of Alcoa (Aluminum Company of America). Its specifications state that its average particle size is about 6.5–8.5 microns and, by hydrometer analysis, 94–99% is below 30 microns, 85–93% is below 20 microns, 56–67% is below 10 microns and 28–40% is below 5 microns. Other typical properties as given by the manufacturer are $Al_2O_3$ 65.0% (64.5% minimum), $SiO_2$ 0.01% (0.02% maximum), $Fe_2O_3$ 0.004% (0.005% max), $Na_2O$ 0.15% (0.25% max), Soluble $Na_2O$ (by Standard Alcoa test methods) 0.02% (0.04% max), moisture (110° C) 0.4% (0.70% max), bulk density (loose) 44 lb./ft.$^3$, bulk density (packed) 77 lb./ft.$^3$, specific gravity 2.42, screen analysis 99% through 325 mesh sieve (98% min.). 25 grams of this material is slurried in 75 grams deionized water and stirred continuously while the pH is measured with a standard meter (using a glass electrode and having a combined reference-and-glass-electrode) in the slurry. Then, while still stirring, 10 ml. of a 5% solution of NaF in deionized water is added. The pH rises rapidly for a few seconds (e.g. about 5 seconds) and then increases more slowly. Before the NaF addition the pH is about 8.5, after such addition it is about 10.5.

Another sample of the same Alcoa C-333 is then treated by mixing it with a 2.0% solution of stearic acid in acetone, the proportions being such as to supply about 1% stearic acid by weight based on the weight of abrasive. Then the acetone is driven off by heating. Although there is some agglomeration of the resulting dry particles, the agglomerates are very friable and break down into individual particles at a touch. When stearic acid-treated material is slurried and tested (in the same manner as described above) the pH values are 6.0 before NaF addition and 6.7 after such addition.

It is noted that the effect of NaF is not dependent on the state of subdivision (and surface area) of the material. For instance when a sample of Alcoa C-31 (an unmilled trihydrate, average particle size about 40 microns) is slurried as indicated (using a 25% slurry) the pH is 7.5; on addition of the NaF it rises to 9.6. Similarly when the Alcoa C-31 is ball-milled in water to subdivide its particles, then washed with water and then made into a 25% slurry with water, its slurry pH is 7.3–7.4; this rises to 10.3 on addition of the NaF.

While not wishing to be bound by any theory it is believed that the stearic acid may react with, or be adsorbed at, positively charged sites on the trihydrate particles or sites presenting aluminum atoms with unsatisfied bonding orbitals, forming a water-resistant aluminum stearate bond. Such reaction or adsorption may also be effected by the use of a soluble salt of stearic acid, such as sodium stearate, which may be included in the toothpaste formulation, as illustrated in Example 2, below.

EXAMPLE 2

A toothpaste is formed by blending 20 parts glycerine, 1.1 parts sodium carboxymethyl cellulose (of conventional dentifrice grade), and 26 parts of an aqueous sodium stearate solution, then adding 0.5 part of benzoic acid, then 52 parts of Alcoa C-333 milled alpha-alumina trihydrate and thereafter 0.24 part of sodium fluoride, as a solid. In this Example the sodium stearate solution is an approximately 4% solution (prepared by mixing 25g deionized water with 0.161g NaOH pellets to form a solution, adding 0.928g of stearic acid and heating to dissolve the latter); thus the sodium stearate concentration is about 1% based on the weight of toothpaste and about 2% based on the weight of trihydrate. The toothpaste shows improved behavior when packaged in unlined aluminum tubes. It does not exhibit gassing or corrosion of the tube walls when packaged in such tubes and stored for a month at 43° C. even though the initial pH of the toothpaste is almost 9. It also shows very good retention of its soluble fluoride content.

It will be understood that the amount of stearic acid or stearate may be reduced considerably, e.g. to ½% or even 0.1% based on the weight of alpha-alumina trihydrate. Also in place of all or part (e.g. ¼, ½ or ¾) of the stearic acid (or stearate) one may use other hydrophobic carboxylic acids such as the long chain fatty acids having about 10 or more (e.g. 10–25) carbon atoms, e.g. lauric, myristic, palmitic or oleic acid or a mixture of such acids, or the corresponding alkali metal salt of such acids or mixtures.

In the formulation in Example II the sodium stearate is present as the sole surface active agent. Other organic surface-active agents, such as those commonly employed in dentifrices, may be included in the formulation to achieve increased prophylactic action, assist in achieving thorough and complete dispersion of the compositions throughout the oral cavity, and render the compositions more cosmetically acceptable. The organic surface active material may be anionic, nonionic, ampholytic or cationic in nature, and it is preferred to employ as the surface-active agent a detersive material which imparts to the dentifrice detersive and foaming properties. Suitable types of such detergents are water-soluble salts of higher (i.e. having at least 12 carbon atoms) fatty acid monoglyceride monosulphates, such as the sodium salt of the monosulphated monoglyceride of hydrogenated coconut oil fatty acids, higher alkyl sulphates, such as sodium lauryl sulphate, alkyl aryl sulphonates, such as sodium dodecyl benzene sulphonate, olefin sulphonates, such as sodium olefine sulphonate in which the olefin group contains 12-21 carbon atoms, higher alkyl sulphoacetates, higher fatty acid esters of 1,2-dihydroxy propane sulphonates, and the substantially saturated higher aliphatic acyl amides of lower (i.e. having not more than 4 carbon atoms) aliphatic amino carboxylic acid compounds, such as those having 12-16 carbons in the fatty acid, alkyl or acyl radicals. Examples of the last mentioned amides are N-lauroyl sarcosine, and the sodium, potassium, and ethanolamine salts of N-lauroyl, N-myristyl or N-palmitoyl sarcosine. The proportion thereof may be in the range of about 0.05 to 3 or 5%, preferably in the range of about ½ to 2%, such as about 1% or 1½%.

Other suitable surface-active materials include non-ionic agents such as condensates of sorbitan monostearate with approximately 60 moles of ethylene oxide, condensates of ethylene oxide with propylene oxide, condensates of propylene glycol ("Pluronics"—PLURONIC is a Trade Mark) and amphoteric agents such as quaternized imidazole derivatives, which are available under the trademark "Miranol" such as Miranol $C_2M$. Cationic surface active germicides and anti-bacterial compounds such as diisobutylphenoxyethoxyethyl dimethyl benzyl ammonium chloride, benzyl dimethyl stearyl ammonium chloride, tertiary amines having one fatty alkyl group (of from 12-18 carbon atoms) and two (poly) oxyethylene groups attached to the nitrogen (typically containing a total of from 20 to 50 ethanoxy groups per molecule) and salts thereof with acids, and compounds of the structure.

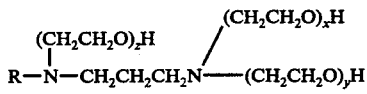

wherein R is a fatty alkyl group typically containing from 12 to 18 carbon atoms, and $x$, $y$ and $z$ total 3 or higher, as well as salts thereof with mineral or organic acids, may also be used.

Examples of amphoteric surface-active compounds are N alkyl beta aminopropionic acid; N alkyl beta imino dipropionic acid; and N alkyl, N,N dimethyl glycine. The alkyl group may be, for example, that derived from coco fatty alcohol, lauryl alcohol, myristyl alcohol (or a lauryl-myristyl mixture), hydrogenated tallow alcohol, cetyl alcohol, stearyl alcohol or blends of such alcohols. The substituted aminopropionic and iminodipropionic and iminodipropionic acids are often supplied in the sodium or other salts forms, which may likewise be used. Examples of other amphoteric agents are betaines containing a sulphonic group instead of the carboxylic group; betaines in which the long chain substituent is joined to the carboxylic group without an intervening nitrogen atom, e.g. inner salts of 2 trimethylamine fatty acids such as 3 trimethyl aminolauric acid, and compounds of any of the previously mentioned types in which the nitrogen atom is replaced by phosphorus.

Particularly suitable added surface-active agents are those which retain good surface-active properties (e.g. foaming) at substantially neutral pH such as the sulfate and sulfonate detergents.

The pH of the toothpaste is preferably within the range of about 5 to 9, e.g. about 6, 7 or 8. It will be noted that the formulation illustrated in Example II above contains also an acidifying agent, specifically benzoic acid, in amount such that (in the absence of the added sodium stearate solution) the pH of the toothpaste would be well below 8 (such as around 6). This may cause conversion of at least part of the sodium soap to the corresponding fatty acid during the toothpaste formulation process.

Milled trihydrate of the particle size suitable for use in dentifrices is commonly made by grinding granules or agglomerates of the trihydrate formed in the Bayer process. The stearic acid (or other hydrophobic fatty acid) may also be introduced during that grinding process. More particularly, in the Bayer process the trihydrate is precipitated, from a solution of sodium aluminate (see Encyclopedia of Chemical Technology, Kirk-Othmer, 2nd Edition, Vol. 1, p. 937-941 and Vol. 2, p. 41-45, 50-51), in the form of granules or agglomerates which are too large for general use as a dentifrice abrasive, e.g. about 40-100 microns diameter. Therefore, the granules or agglomerates after drying (sometimes after water-washing and drying) are ground to a suitable particle size, e.g. to an average particle diameter in the range of about 2 to 20 microns, such as about 5 to 10 microns diameter. The grinding of the trihydrate in the presence of the acid may be practiced using techniques and apparatus recognised in the art. For instance, ball milling is described in "Surface Activity in Fine Dry Grinding" Berry & Kamack, pages 196-202, in Solid/Liquid Interface; Cell/Water Interface (Biological) Vol. 4. Edited by J. H. Schulman (Proceedings of the Second International Congress on Surface Activity, London, 1957) Academic Press, New York, 1958, "Grinding Low-Soda Alumina" by Hart and Hudson, Ceramic Bulletin, Vol. 43, No. 1 (1964); and U.S. Pat. No. 3,358,937 granted Dec. 19, 1967; Vibrative-Energy Milling is described in the article by Hart & Hudson and Pin-type Milling is described in Perry, Chemical Engineers' Handbook, 5th Edition, 1973, pages 8-37 to 8-71.

The added acid may be incorporated into the trihydrate being fed to the mill, may be metered into the mill itself during operation or may be added to the wet slurry before grinding. It is also within the broad scope of the invention to add the surface modifying agent to the size classification zone associated with the mill. Thus it is common to pass the product of the mill to a size classification zone (e.g. a cyclone) from which the oversize, insufficiently ground, particles are returned to the mill for further grinding. Co-grinding with surface modifying agent is the subject of U.S. application Ser. No. 640,663 filed Dec. 15, 1975 claiming priority of British Provisional Specification 53932 of Dec. 13, 1974 of Baines and Carr.

The aqueous vehicle of the dentifrice may include sources of fluoride ions such as sodium fluoride, stannous fluoride, manganese fluoride, potassium fluoride, lithium fluoride, ammonium fluoride and complex fluorides, particularly alkali metal monofluorophosphates. The fluorine-containing compound is employed in amount which provides an effective non-toxic amount of fluorine-containing ion to the dentifrice, typically 0.01%-1% by weight preferably about 0.1% fluorine. Thus sodium fluoride is typically employed in amount of 0.02-2% by weight, preferably about 0.2%, and sodium monofluorophosphate, $Na_2PO_3F$, in amount of 0.1-7.6% by weight, preferably about 0.8%.

The alkali metal monofluorophosphates which may be employed include sodium monofluorophosphate, lithium monofluorophosphate, potassium monofluorophosphate and ammonium monofluorophosphate. The preferred salt is sodium monofluorophosphate, $$Na_2PO_3F,$$

which, as commercially available, may vary considerably in purity. It may be used in any suitable purity provided that any impurities do not substantially adversely affect the desired properties. In general, the purity is desirably at least 80%. For best results, it should be at least 85%, and preferably at least 90% by weight of sodium monofluorophosphate with the balance being primarily impurities or by-products of manufacture such as sodium fluoride and water-soluble sodium phosphate salt. Expressed in another way, the sodium monofluorophosphate employed should have a total fluoride content of above 12%, preferably above 12.7%, a content of not more than 1.5%, preferably not more than 1.2% of free sodium fluoride; and a sodium monofluorophosphate content of at least 12%, preferably at least 12.1% all calculated as fluorine.

Other monofluorophosphate salts which may be used in the invention include monofluoropolyphosphates such as

| | |
|---|---|
| $Na_4P_3O_9F,$ | $Na_3KP_3O_9F,$ |
| $K_4P_3O_9F,$ and | $(NH_4)_3NaP_3O_9F$ |
| $(NH_4)_4P_3O_9F,$ | $Li_4P_3O_9F.$ |

The aqueous vehicle of the dentifrice preferably forms a mass of a consistency which desirably can be extruded from a collapsible tube such as an aluminium tube or a lead tube. The vehicle will generally contain liquids and solids. In general, the liquid portion comprises water, glycerine or aqueous sorbitol, including suitable mixtures thereof. It is usually advantageous to use a mixture of both water and a humectant such as glycerine or sorbitol. The total liquid content is generally 20–94.5% by weight of the dentifrice and typically includes up to 30% by weight of water, 0–80% by weight of glycerine and 0–80% by weight of sorbitol. Preferably up to 20% by weight of water, 15–40% by weight of glycerine and 0–50% by weight of sorbitol are present in the dentifrice.

The solid portion of the vehicle may be a gelling agent, such as the natural and synthetic gums and gum-like materials, such as Irish Moss, gum tragacanth, alkali metal carboxymethyl cellulose and hydroxyethyl carboxymethyl cellulose, polyvinyl pyrrolidone, starch, water soluble, hydrophilic colloidal carboxyvinyl polymers, such as those sold under the trademark Carbopol 934 and 940 and synthetic inorganic silicated clays such as those sold under the trademark Laponite CP and Laponite SP. These grades of Laponite have the formula $$[Si_8Mg_{5.1}Li_{0.6}H_{7.6}O_{24}]0.6-_{Na}+_{0.6}.$$

The solid portion of the vehicle is typically present in amount up to 10% by weight of the dentifrice and preferably 0.5–5% by weight. When employed, grades of Laponite are preferably used in amounts of 1–5% by weight.

Any suitable flavouring or sweetening materials may be employed in formulating a flavour for the dentifrice. Examples of suitable flavouring constituents include flavouring oils, e.g. oils of spearmint, peppermint, wintergreen, sassafras, clove, sage, eucalyptus, marjoram, cinnamon, lemon and orange, as well as methylsalicylate. Suitable sweetening agents include sucrose, lactose, maltose, sorbitol, perillartine and saccharine. Suitably, flavour and sweetening agents may together constitute from 0.01 to 5% or more of the dentifrice. Chloroform may also be used.

Various other materials may be incorporated in the dentifrices Examples thereof are colouring or whitening agents or dyestuffs, preservatives, silicones, chlorophyll compounds, ammoniated materials such as urea, diammoniumphosphate and mixtures thereof, and other constituents. The adjuvants are incorporated in the compositions in amounts which do not substantially adversely affect the properties and characteristics desired.

Antibacterial agents may also be present, typically in an amount of 0.01–5% by weight. Typical antibacterial agents include $N^1$-(4-chlorobenzyl)-$N^5$-(2,4-dichlorobenzyl)biguanide;
p-chlorophenyl biguanide;
4-chlorobenzhydryl biguanide;
4-chlorobenzhydrylguanylurea;
N-3-lauroxypropyl-$N^5$-p-chlorobenzylbiguanide;
1,6-di-p-chlorophenylbiguanidohexane;
1,6-dis(2-ethylhexylbiguanido)hexane;
1-(lauryldimethylammonium)-8-(p-chlorobenzyl-dimethylammonium) octane dichloride;
5,6-dichloro-2-guanidinobenzimidazole;
$N^1$-p-chlorophenyl-$N^5$-laurylbiguanide;
5-amino-1,3-bis(2-ethylhexyl)-5-methylhexahydro pyrimidine;

and their non-toxic acid addition salts.

Other dentifrice ingredients may also be present if desired, in appropriate conventional proportions.

In a more general aspect, this development relates to the protection of the surfaces of the particles of abrasive in the dentifrice to reduce the chemical activity of the surfaces thereof, e.g. to prevent or hinder passage of components of the abrasive into the aqueous medium of the dentifrice, this protection being effected by means of a surface treatment with a water-insoluble material that adheres to active sites of said particles. Preferably the material is hydrophobic. The treating material is preferably capable of being applied in liquid phase even though it need not necessarily be liquid at room temperature. For example, a waxy or high viscosity greasy material may be applied in a solvent (e.g. a volatile solvent) or at an elevated temperature at which it is in a sufficiently fluent liquid phase. The abrasive particles are usually up to about 50 microns, e.g. 2 to 30 microns, in average diameter and the treating material is used in such small amounts as to furnish a protective barrier without substantially adversely affecting the character or quality of the abrasive for the toothpaste, and preferably without altering the physical form of the particles. The treated abrasive particles may be maintained in substantially unagglomerated form so that treated abrasive particles are individually invisible when compounded into a toothpaste as contrasted to visible agglomerate speckles. The treating material can be mixed with the abrasive particles before mixing with other ingredients of the dentifrice as described. Alternatively, the treating material can be applied to the abrasive in the presence of other ingredients of the dentifrice under conditions such that the affinity of the treating material to the abrasive surfaces is maintained.

The phenomenon can be regarded as a form of microencapsulation of the abrasive particles. The layer of treating material may be very thin, e.g. of monomolecular thickness. Indeed, it is desirable that the layer of coating material should be as thin as possible consistent with its protective function, so that it does not appreciably diminish the abrasive action of the dentifrice when the teeth are brushed with it.

Various treating materials can be used, which can be polar or non-polar.

Some such materials have been proposed for inclusion in dentifrices for different purposes and in circumstances such that they would not effectively treat abrasive particles present in the dentifrices.

A special embodiment relates to the use of polar materials including, for example higher ($C_8$–$C_{22}$) fatty alcohols and higher fatty acids, such as lauric and stearic acids and lauryl and stearyl and alcohol. Such polar materials should be chosen so that they have an affinity for the particular abrasive material employed, e.g. the active end of the molecule is attached to the abrasive material and the long hydrocarbon chain affords hydrophobic properties.

Suitable non-polar materials include waxes, vegetable oils such as palm oil and hydrogenated palm oil, and hydrocarbon oils and greases, e.g. mineral oils such as liquid paraffin, e.g. light or heavy petrolatum, petroleum jelly and petroleum wax.

In a broader aspect of the development the treating agent may be a surface-active agent, e.g. of the cationic or amphoteric categories, previously mentioned.

The amount of the coating or treating material employed will vary depending on a number of factors, such as the particle size of the abrasive and its specific surface area. As indicated, the quantity may be sufficient to provide a layer of at least monomolecular thickness, but not so much as to effect adversely the desired properties of the dentifrice. In general, amounts in the range from 0.1% to 5%, such as 0.5, 1, 2 or 3% by weight based on the weight of abrasive, will be suitable. Typically the amount will be less than 5% by weight of the dentifrice.

Examples of abrasives include calcium carbonate, magnesium carbonate, tricalcium phosphate, dicalcium phosphate dihydrate, insoluble sodium metaphosphate, calcium pyrophosphate, aluminium hydroxide, alumina (including alpha alumina trihydrate), synthetic amorphous complex alumina silicates, silica (including dehydrated silica gels). The amount of abrasive will usually be in the range from 5 to 60%, preferably from 15 to 50%, by weight of the dentifrice.

It will be understood that it will be desirable to make preliminary trials with any particular combination of encapsulating agent and abrasive to obtain best results. For instance, simple treatment of abrasive with the encapsulating agent may result, when the encapsulated material is placed in a particular environment, in release of the agent from the abrasive; this occurred when alpha-alumina trihydrate was treated with a mineral oil solution and then placed in water. Combinations of encapsulating agents (e.g. stearic acid plus mineral oil), or successive treatments with different encapsulating agents, may be employed with a view to improving the surface-bonding of the encapsulating material.

|  | Example Number |  |  |  |  |  |  |
|---|---|---|---|---|---|---|---|
|  | 3 | 4 | 5 | 6 | 7 | 8 | 9 |
| Encapsulated Abrasive (Note 1) |  |  |  |  |  |  |  |
| Dicalcium phosphate dihydrate | 48.0 | — | — | 40.0 | 33.0 | — | 48.0 |
| Alpha alumina trihydrate | — | 52.0 | — | — | 15.0 | 15.0 | — |
| Precipitated calcium carbonate | — | — | 48.0 | 8.0 | — | 33.0 | — |
| Humectant (Note 2) |  |  |  |  |  |  |  |
| Glycerin | 22.0 | 20.0 | 22.0 | 22.0 | 22.0 | 22.0 | 22.0 |
| Thickener |  |  |  |  |  |  |  |
| Carboxymethyl cellulose | 1.0 | 1.0 | 1.0 | 1.0 | 1.0 | 1.0 | — |
| Hydroxyethyl cellulose | — | , | — | — | — | — | 1.1 |
| Flavour and Sweetener |  |  |  |  |  |  |  |
| Flavour | 0.8 | 0.8 | 0.8 | 0.8 | 0.8 | 0.8 | 0.8 |
| Sodium saccharinate | 0.2 | 0.2 | 0.2 | 0.2 | 0.2 | 0.2 | 0.2 |
| Detergent (Note 3) |  |  |  |  |  |  |  |
| Sodium lauryl sulphate | 1.5 | 1.5 | 1.5 | 1.5 | 1.5 | 1.5 | — |
| Nonionic or amphoteric detergent (e.g. Miranol C2M) | — | — | — | — | — | — | 1.5 |
| Prophylactic agent |  |  |  |  |  |  |  |
| Sodium monofluorophosphate | — | — | 0.1 | 0.1 | 0.2 | 0.2 | — |
| Sodium fluoride | — | — | 0.1 | 0.1 | 0.2 | 0.2 | — |
| chlorhexidine digluconate | — | — | — | — | — | — | 0.5 |
| Water | q.s. | q.s | q.s | q.s | q.s | q.s | q.s |

-continued

|   | Example Number | | | | | | |
|---|---|---|---|---|---|---|---|
|   | 3 | 4 | 5 | 6 | 7 | 8 | 9 |
|   | to 100 in each case | | | | 43 | 43 | 43 | 43 |

(Note 1)
In each case the surfaces of the abrasive particles are pre-treated with 1% stearic acid as previously described (as by applying a solution of the treating agent in a solvent therefor and then evaporating the solvent). In several modifications of these Examples the abrasive particles are precoated with liquid paraffin, palm oil, hydrogenated palm oil, lauryl alcohol and stearyl dimethyl ammonium chloride. In other modifications the abrasives, without pre-treating, are blended with other ingredients of the dentifrice except for the detergent, which is mixed with the blend later.

(Note 2)
In modifications of each of the Examples, about 50% of the glycerin is replaced by sorbitol.

(Note 3)
In modifications of each of the Examples the sodium lauryl sulphate is replaced by sodium N-lauryl sarcosinate.

We claim:

1. Toothpaste comprising an aqueous vehicle and about 5 to 60% of dental abrasive particles of about 2 to 20 microns diameter individually dispersed therein, said particles comprising milled alpha-alumina trihydrate which has been surface-treated with about 0.1 to 2%, based on the weight of said milled trihydrate, of a hydrophobic long chain fatty carboxylic acid having 10 to 25 carbon atoms or a mixture of said acids, said toothpaste having a pH of about 5 to 9 and being in an unlined aluminum tube.

2. Toothpaste as in claim 1 in which sodium fluoride is dispersed in said vehicle.

3. Toothpaste as in claim 1 in which the proportion of said acid is in the range of about 0.1 to 2% based on the weight of alpha-alumina trihydrate.

4. Toothpaste as in claim 1 in which said alpha-alumina trihydrate has been contacted with said acid before mixing said particles with said vehicle.

5. Toothpaste as in claim 1 in which said vehicle contains said acid or a mixture of said acids or an alkali metal salt of said acid or mixture of acids.

6. Toothpaste comprising an aqueous vehicle containing a hydrophobic long chain fatty carboxylic acid having 10 to 25 carbon atoms or a mixture of said acids or an alkali metal salt of said acid or mixture of acids and containing about 5 to 60% of dental abrasive particles comprising milled alpha-alumina trihydrate of about 2 to 20 microns diameter individually dispersed in said vehicle, the amount of said acid being about 0.1 to 2% based on the weight of said milled trihydrate, said toothpaste having a pH of about 5 to 9 and being in an unlined aluminum tube.

7. Toothpaste as in claim 6 in which said vehicle contains sodium stearate in amount of about 0.1 to 2% based on the weight of alpha-alumina trihydrate.

* * * * *